United States Patent [19]

De Lacy

[11] 3,939,698
[45] Feb. 24, 1976

[54] METHOD AND APPARATUS FOR MEASURING POROSITY USING A SURFACE-TEMPERATURE POROSIMETER

[75] Inventor: Thomas J. De Lacy, La Mesa, Calif.

[73] Assignee: General Dynamics Corporation, San Diego, Calif.

[22] Filed: May 23, 1974

[21] Appl. No.: 472,572

[52] U.S. Cl. .................................... 73/73; 73/15.4
[51] Int. Cl.² ....................................... G01N 15/08
[58] Field of Search ........... 73/38, 15 R, 15.4, 17 A, 73/190 R, 73, 432 PS, 61.3

[56] References Cited
UNITED STATES PATENTS

| | | | |
|---|---|---|---|
| 2,477,526 | 7/1949 | Perley | 73/15 R |
| 3,712,110 | 1/1973 | Paulik et al. | 73/15 B |
| 3,733,893 | 5/1973 | Bickford et al. | 73/73 |

OTHER PUBLICATIONS

Hirst, et al., "A Calorimeter for the Measurement of Small Amounts of Heat Liberated Slowly", Scientific Instruments, Vol. 27, June 1950 pp. 161–163.

Kazanskii, et al., "Determination of the Specific Heat of Evaporation of a Liquid from Dispersed Solids in a Wide Temperature Range", J. Engineering Physics, Vol. 11, No. 5, Nov. 1966, pp. 328–332.

Primary Examiner—Charles A. Ruehl
Attorney, Agent, or Firm—John R. Duncan

[57] ABSTRACT

A method and apparatus for measuring the porosity or density of a porous structure surface is disclosed. A controlled quantity of volatile liquid is applied to a porous surface and is allowed to evaporate. The temperature at the surface reaches equilibrium at the point necessary to supply the latent heat of vaporization of the liquid. This equilibrium temperature depends on the evaporation rate, which has been found to be a function of surface porosity. The porosimeter substantially eliminates other factors influencing evaporation rate, and measures and records the temperature at the surface. Once calibrated with samples of known porosity, this system is capable of making rapid, accurate surface porosity measurements.

6 Claims, 2 Drawing Figures

METHOD AND APPARATUS FOR MEASURING POROSITY USING A SURFACE-TEMPERATURE POROSIMETER

BACKGROUND OF THE INVENTION

This invention relates in general to a method and apparatus for measuring surface porosity and, more specifically, to a novel surface-temperature porosimeter.

Materials having selected surface porosities are in use in a variety of applications. In many cases, it is necessary that the surface porosity be carefully maintained within a limited range. Examples of such materials include foam insulation for cryogenic applications, graphite ablative materials, protective coatings, etc. A non-destructive porosity measuring technique would be a very helpful quality control aid in assuring that porosity of insulation coatings, ablative heat shields, etc. on production structures is within the required range.

Prior art porosity techniques generally require removal of samples of the material and testing in complex laboratory apparatus. These techniques are slow and cumbersome and do not permit testing of actual production materials in place.

Thus, there is a continuing need for improved porosity measuring systems.

It is, therefore, an object of this invention to provide a porosimeter overcoming the above-noted problems.

Another object of this invention is to provide a non-destructive method of determining porosity.

A further object of this invention is to provide a method and apparatus for determing the relative density, porosity and pore spectra of materials.

SUMMARY OF THE INVENTION

The above objects, and others, are accomplished in accordance with this invention by a system in which a quantity of a volatile liquid is applied to a surface and allowed to evaporate while the temperature of the surface is continuously measured. This temperature reaches equilibrium at the point necessary to supply the latent heat of vaporization of the liquid. This equilibrium temperature depends on the evaporation rate. The liquid when applied is absorbed by pores in the structure. As the liquid evaporates, the liquid at the surface is replenished by capillaries attributable to open porosity and the volume of retained liquid so that evaporation rate and time and the resulting surface equilibrium temperature are functions of surface porosity.

Since the evaporation rate is determined in part by the temperature of the air surrounding the surface, the porosimeter preferably includes an insulated chamber maintained at a substantially constant temperature around the surface area being tested. Also, it is desirable to include means for preventing vapor buildup which may reduce the evaporation rate of the liquid.

Any suitable liquid may be used in this system. The liquid should be sufficiently volatile to evaporate in a reasonable time at the temperature being maintained in the system, which ordinarily will be near room temperature. The liquid should not dissolve or otherwise degrade the material being tested. Typical liquids useful with many porous materials include low molecular weight alcohols, dichloro methane, carbon tetrachloride, water and mixtures thereof.

The liquid may be applied to the surface in any suitable way. Where small blocks are being tested, the block may be placed in a dish containing a shallow pool of liquid. For larger surfaces, often spraying or feeding a stream of liquid through a metering valve may be preferred.

BRIEF DESCRIPTION OF THE DRAWING

Further details of the invention, and of a preferred embodiment of the invention, will be further understood upon reference to the drawing, wherein.

DETAILED DESCRIPTION OF THE INVENTION

Figure 1:
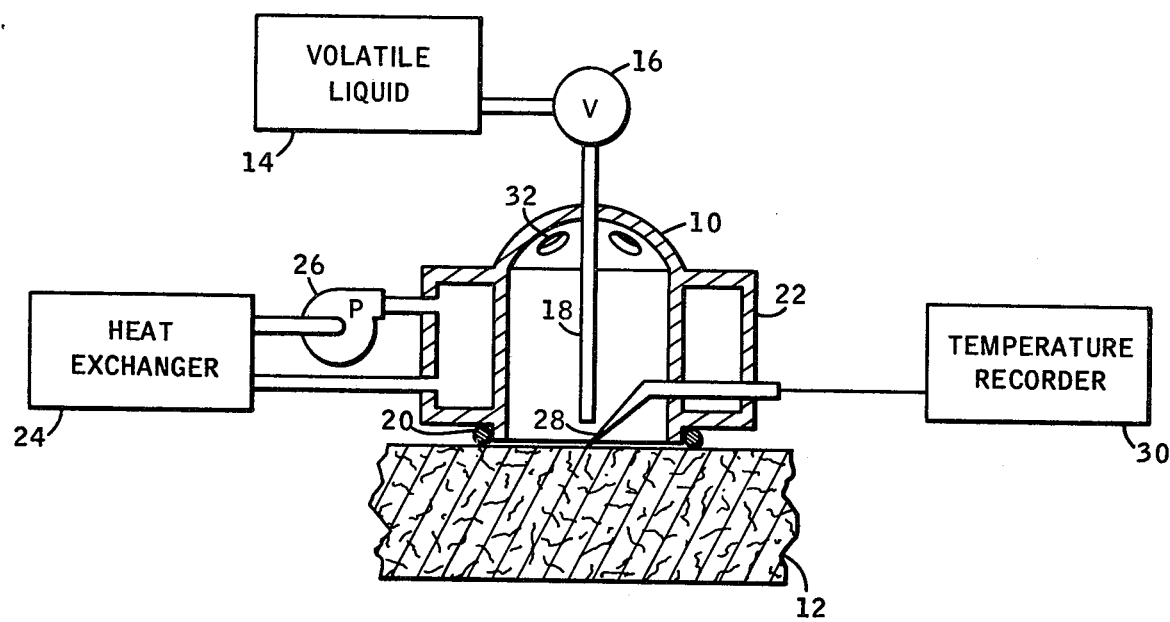
FIG. 1 shows a schematic diagram illustrating the porosimeter of this invention.

Referring now to FIG. 1, there is seen a schematic block diagram illustrating the porosimeter of this invention. The porosity measuring assembly is enclosed within a generally bell-shaped chamber 10 which is placed with the open end in contact with the structure surface 12 to be tested.

The selected volatile liquid is fed from a reservoir 14 through a feeding means 16 to a tube 18 which deposits the liquid on the surface of structure 12 near the center of chamber 10. As mentioned above, any suitable volatile liquid which is compatible with the composition of structure 10 may be used. Preferably, the same quality of liquid is applied when calibrating the system with structures of known porosity and then with test structures of unknown porosity. Where reservoir 14 is calibrated in the manner of a graduate cylinder, feeding means 16 may be a stopcock or similar valve allowing the selected quantity as measured at reservoir 14 to flow by gravity to tube 18. Alternatively, feeding means 16 could be a metering pump which would spray a selected quantity of liquid onto the surface of structure 12. If structure 12 is small in size, the test surface could be immersed in a shallow pool of liquid, then placed in contact with chamber 10. While gravity feed of a measured amount of liquid is preferred for simplicity and accuracy, any other suitable liquid application technique may be used, if desired.

Preferably, a sealing means 20, typically an "O" ring, is placed around the contact ring between chamber 10 and structure 12 to protect against varying air leaks therebetween which might affect the evaporation rate at the nearby liquid test area.

Since the evaporation rate is influenced by the temperature of the air surrounding the surface, it is preferred that chamber 10 be maintained at a substantially constant temperature. This may be accomplished by a water jacket 22 surrounding chamber 10. A liquid, such as water, at a selected temperature, is circulated between water jacket 20 and a heat exchanger 24 by pump 26.

Figure 2:
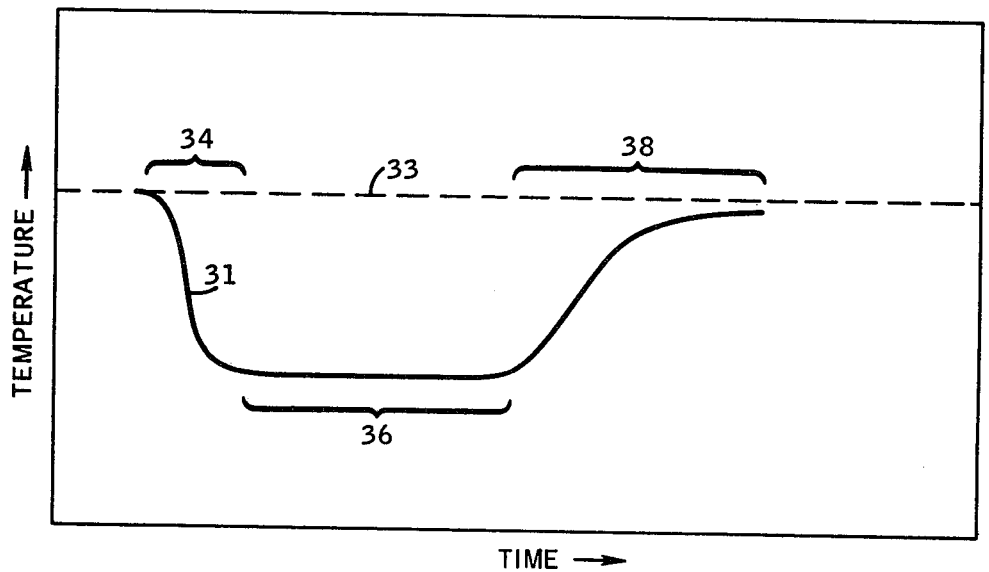
FIG. 2 shows a curve of temperature plotted against time for the measurement of porosity.

The temperature at the surface of structure 12 is continuously monitored. Typically, a thermocouple 28 may extend through the wall of chamber 10 into contact with the surface of structure 12 at the spot where the volatile liquid is applied. The temperature is recorded by a recorder 30 which provides a plot of temperature against time of the sort illustrated in FIG. 2.

Since the buildup of vapor within chamber 10 as the test liquid evaporates may reduce the evaporation rate, chamber 10 is preferably vented, such as by vents 32.

Since the amount of liquid is ordinarily quite small, vapor buildup is not ordinarily a significant problem. However, if desired, air at chamber temperature may be pumped through chamber 10 at a low rate to carry off excess vapor.

The porosimeter schematically illustrated in FIG. 1 can be assembled into a small, portable unit which can be taken wherever desired to measure the porosity of coatings, insulation, etc., on large structures. Once the characteristics of samples of known porosity are measured, the porosity of an unknown porosity sample of the same composition can be quickly determined.

In a typical measuring operation, chamber 10 is placed in contact with the surface of a structure of known or unknown porosity. Heat exchanger 24 and pump 26 are operated to bring the temperature within chamber 10 to a stable selected temperature which ordinarily will be close to the structure temperature under the existing ambient conditions. Temperature recorder 30 is activated and a measured quantity of liquid is applied to the structure surface through tube 18. As shown by curve 31 in FIG. 2, the temperature measured by thermocouple 28 initially drops rapidly from ambient temperature 33 over time span 34, then levels off when the volume of liquid returning to the surface from large pores feeding capillaries within the structure equals that being evaporated. The temperature remains substantially constant for time period 36 until these subsurface reservoirs are exhausted, at which time (as shown at 38) the temperature rises as the liquid in the capillaries is depleted and the surface returns to ambient temperature. The time periods 36 and 38 are shorter for more dense materials and longer for more porous materials. By running a series of tests with samples of a single composition of different porosity, a series of curves similar to that shown in FIG. 2 can be developed. Then, a curve for a sample of the same compoisition but unknown porosity can be compared to the standard curves to nondestructively determine the porosity of the unknown sample. Comparison of curves for known and unknown porosity may be accomplished by comparing the shape of the curves, the length of time periods 34, 36 and 38, or by integrating the area between curve 31 and ambient temperature 33. Generally, the most accurate results are obtained by comparing the curves produced during time period 38, or by comparing equilibrium temperatures for controlled liquid volumes which penetrate the surface.

Details of several preferred embodiments of the method of this invention will be further described in the following examples. Parts and percentages are by weight unless otherwise stated.

EXAMPLE I

Four blocks of polyurethane foam of the type used for cryogenic tank insulation having densities of 0.422, 0.460, 0.498 and 0.536 g/cm³ and one having an unknown density are prepared. The first block is placed in contact with a test chamber of the sort shown in FIG. 1 and a heat exchanger circulating water around the chamber is activated to bring the chamber to a uniform 20°C. A chromel-alumel thermocouple is placed in contact with the foam near the center of the chamber and is connected to a single channel strip chart recorder, available from Honeywell, Inc. A reference junction is provided for absolute measurement. About 0.5 ml. of dichloro methane is fed into the chamber and dropped onto the foam surface at the point of thermocouple contact. The recorder traces a a curve of time against temperature similar to that shown in FIG. 2. The other four foam samples are then tested in the same manner. The area between the ambient temperature line and the curve, and the time to return to substantially ambient temperature, are found to decrease with increasing density through the four known samples. The curve for the unknown sample is compared to the four known sample curves. The unknown curve falls between the curves for the 0.422 and 0.460 g/cm³ curves, indicating that the density of the unknown sample is about 0.440 g/cm³.

EXAMPLE II

Two molded graphite blocks having densities of 1.80 and 1.60 g/cm³ are prepared. A small quantity of ethyl alcohol is placed in a shallow dish and a block is placed in the dish. After about 5 seconds, the block is removed and placed in the test apparatus described in Example I. As the alcohol evaporates, the recorder plots a time/temperature curve similar to that shown in FIG. 2. The test is repeated with the second block, producing a second curve. Then a third block having an unknown density is tested in the same manner. Comparison of the three curves indicates the density of the unknown block to be about 1.72 g/cm³. Later density measurements show this density test to be accurate within about ±0.01 g/cm³.

EXAMPLE III

Two sheets of polyphenylene oxide foam, available from General Electric under the PPO trademark, are prepared. The sheets have densities of about 0.536 and 0.460 g/cm³. An iron-constantan thermocouple connected to a strip chart recorder is placed in contact with each sheet. About 0.1 ml. of methyl chloride is sprayed on each sheet in the area of thermocouple contact. A hemispherical cover maintained at about 68°F is placed over each test area and a stream of air at about 68°F is passed slowly through ducts connected to the cover. Each recorder produces a curve similar to that shown in FIG. 2. The surface temperature drops to about 20°F, then after a stable period returns to ambient temperature. This stable period is much shorter, and thus the evaporation rate more rapid, in the more dense specimen.

EXAMPLE IV

Six standard test blocks of open cell silicon foam of known different densities and one sheet of unknown density are tested using a surface temperature porosimeter of the type illustrated in FIG. 1. The blocks and chambers are heated to about 90°C. About 0.5 ml. of distilled water is applied to the surface of each block at the point where a chromel-alumel thermocouple contacts the block. The termperature at that point is recorded on a strip chart recorder for each block. Examination of the shapes of the curves of the known density blocks indicates a correlation between curve and density, and indicates that the unknown block has a surface density of about 0.40 g/cm³. This is later verified by mechanical measurement.

EXAMPLE V

Five test blocks having painted surfaces with micropore distribution ranging between 0.1 and 10 volume percent are tested together with a painted surface having an unknown pore spectra. Each block is tested with a device of the sort shown in FIG. 1. About 0.1 ml. of low molecular weight alcohol is applied to the surface of each block. A copper-constantan thermocouple is held in contact with each painted surface as the alcohol is evaporated. The evaporation temperature/time curve is recorded for each test surface using a multi-channel strip recorder. The test is repeated for the unknown sample. By comparison of the curves, the pore spectra of the unknown surface is found to correspond to a standard which indicates that the painted surface porosity is greater than permitted for the application. The surface is, therefore, stripped and repainted. A re-test of the surface indicates the pore spectra to now be within acceptable limits.

Specific materials, components and mechanical arrangements have been detailed in the above description of preferred embodiments. These may be varies and other components may be used where suitable. Other variations, applications and ramifications of the invention will become apparent to those skilled in the art upon reading this disclosure. These are intended to be included within the scope of this invention, as defined in the appended claims.

I claim:
1. A porosimeter comprising:
    means to supply a selected quantity of volatile liquid to a point on a porous structure surface;
    a chamber in contact with said surface surrounding said point to maintain the space adjacent to said point within said chamber at a substantially constant temperature;
    temperature measuring means in contact with said surface at said point; and
    recording means for recording temperature over a time period after said liquid is applied at said point.
2. The porosimeter according to claim 1 further including means permitting removal from said space of vapors resulting from evaporation of said liquid.
3. The porosimeter according to claim 1 wherein said temperature measuring means comprises a thermocouple in contact with said surface at said point.
4. The porosimeter according to claim 1 wherein said chamber including a jacket through which a liquid at substantially constant temperature is passed.
5. The method of measuring the surface porosity of a structure which comprises:
    applying a selected quantity of a volatile liquid to a point on a porous structure surface;
    maintaining the space adjacent to said surface near said point at a substantially constant temperature;
    continuously measuring the temperature of said surface at said point;
    continuously recording the temperature over a time period after said liquid is applied to said surface.
6. The method according to claim 5 comprising the further step of comparing the recorded time-temperature relationship to similar relationships developed by applying the method of claim 5 to a plurality of structures of the same composition but known different porosities to determine the porosity of this structure.

* * * * *